United States Patent [19]

Jessop et al.

[11] 4,420,566
[45] Dec. 13, 1983

[54] METHOD AND APPARATUS FOR DETECTING SAMPLE FLUID ON AN ANALYSIS SLIDE

[75] Inventors: Thomas C. Jessop, Webster; Donald De Jager, Rochester, both of N.Y.

[73] Assignee: Eastman Kodak Company, Rochester, N.Y.

[21] Appl. No.: 387,124

[22] Filed: Jun. 10, 1982

[51] Int. Cl.$^3$ .................... G01N 35/00; G01N 35/06; G01N 21/00; G01N 33/18
[52] U.S. Cl. .................... 436/46; 250/339; 250/341; 422/63; 422/66; 422/67; 422/100; 436/44; 436/39; 436/164
[58] Field of Search ................ 250/339, 341; 422/63, 422/66, 67, 55–58, 101, 100; 23/230 R, 230 B; 436/43, 46, 39, 164, 44

[56] References Cited

U.S. PATENT DOCUMENTS

| | | | |
|---|---|---|---|
| 3,405,268 | 10/1968 | Brunton | 250/339 |
| 4,059,405 | 11/1977 | Sodickson | 23/230 R |
| 4,110,079 | 8/1978 | Schaeffer | 422/56 |
| 4,203,724 | 5/1980 | Sawai et al. | 23/230 B |
| 4,224,032 | 9/1980 | Glover et al. | 435/809 |

*Primary Examiner*—Michael S. Marcus
*Attorney, Agent, or Firm*—D. D. Schaper

[57] ABSTRACT

A method and apparatus are disclosed for detecting sample fluid on an analysis slide of the type which is used to perform quantitative analyses. The apparatus comprises means for projecting radiation comprising wavelengths absorbed by water onto the slide and means for measuring the intensity of radiation received from the slide, both before fluid is metered on the slide and after fluid has been metered thereon. The difference between radiation received from a wet slide and from a dry slide is compared with known values to determine if the slide contains sufficient fluid for a suitable test result.

20 Claims, 10 Drawing Figures

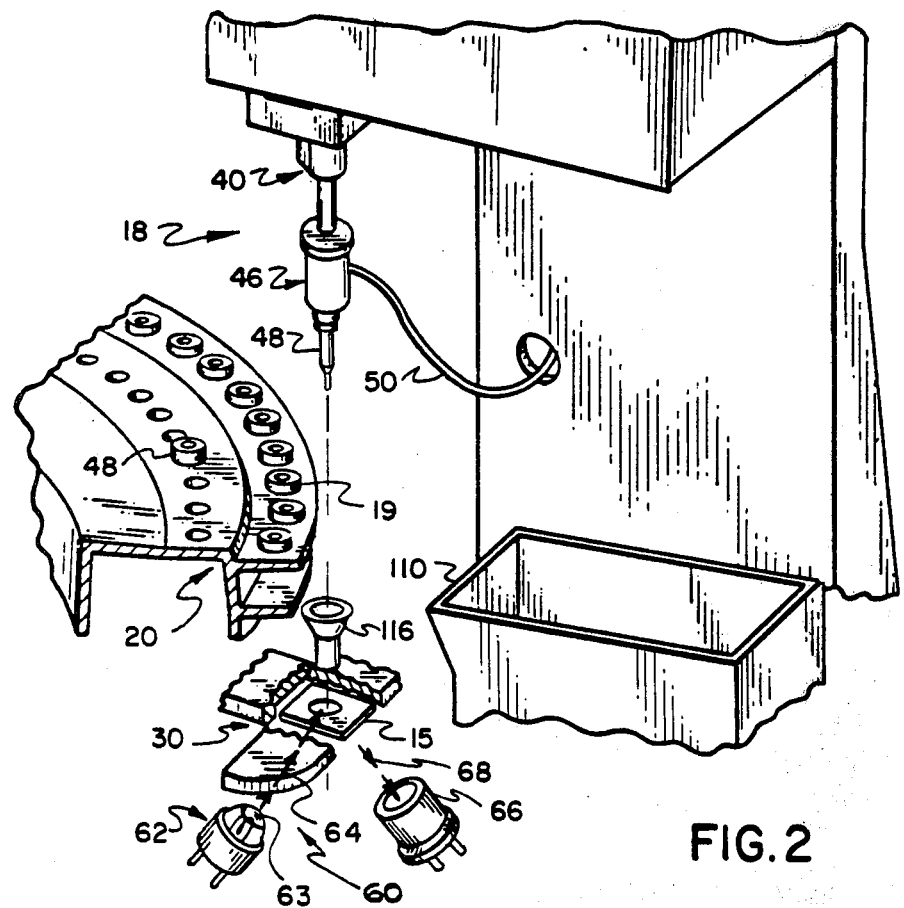
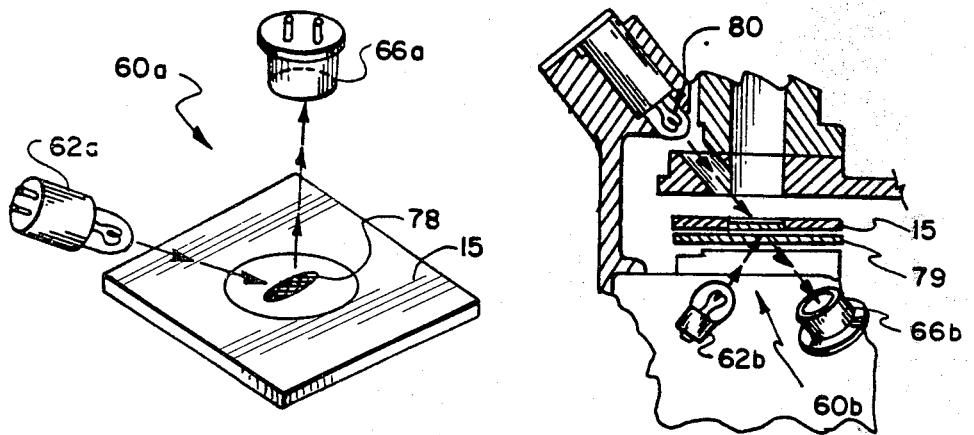
FIG. 2
FIG. 3
FIG. 4

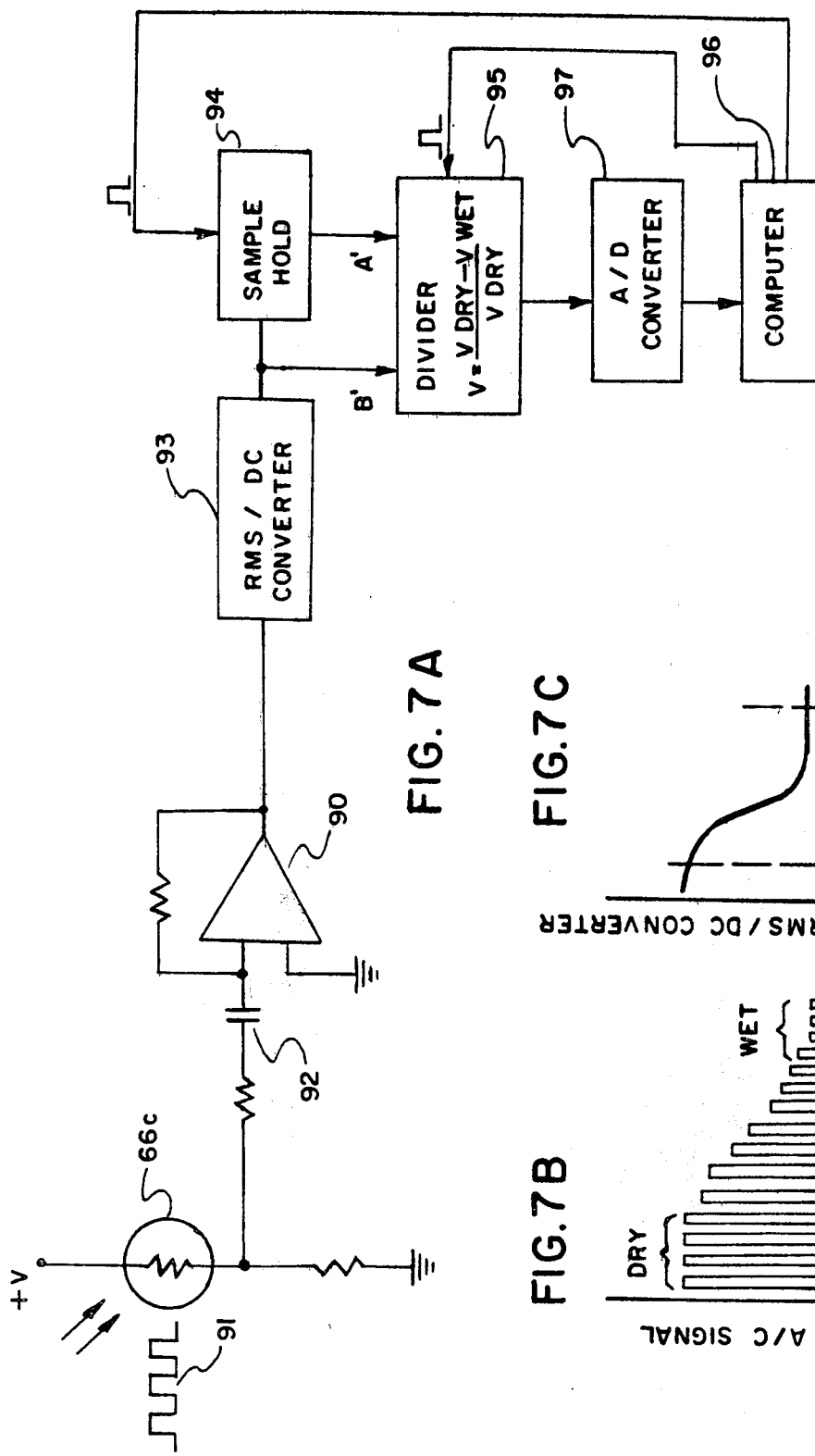

METHOD AND APPARATUS FOR DETECTING SAMPLE FLUID ON AN ANALYSIS SLIDE

CROSS-REFERENCE TO RELATED APPLICATIONS

This application is a continuation-in-part of U.S. Pat. application Ser. No. 299,682, filed Sept. 8, 1981, now abandoned. Reference is made to commonly-assigned U.S. Pat. application Ser. No. 260,855, entitled METHOD AND APPARATUS FOR METERING BIOLOGICAL FLUIDS, filed in the name of Collins et al., on May 6, 1981.

BACKGROUND OF THE INVENTION (1) Field of the Invention

This invention relates to the detection of sample fluid on an analysis slide of the type which is adapted to receive a predetermined quantity of sample fluid and to produce a response proportional to a selected analyte in the fluid. More particularly, the invention relates to a method and apparatus for determining whether a sufficient amount of fluid has been metered onto the analysis slide to produce a suitable response.

(2) State of the Prior Art

Recent developments have provided generally planar analysis slides which are used for the detection of selected analytes in biological fluids. The slides are adapted to be used in automatic high-throughput analyzers. In the processing of such slides, a predetermined amount of biological fluid, for example 10 microliters, is metered onto the slide, and a reflectance reading of the slide is taken after a suitable incubation period. The volume of fluid metered onto the slide must be controlled within certain limits to obtain acceptable test results. Thus, it is important to know if the metering apparatus is functioning within these limits.

Metering devices, for use in clinical apparatus, are adapted to expel fluid from a metering tip by means of a pressure system. One method of determining whether a metering device is functioning properly is to monitor the pressure change in the system as the fluid is being metered. It has been found, however, that such a method is not sufficiently sensitive for the precision tests being performed in most analyzers. Further, this method does not detect whether or not the fluid has been deposited in the proper area of the analysis slide. A metering device having a pressure detector of the type described is disclosed in U.S. Pat. No. 4,041,995.

Devices for measuring the moisture content of sheet material, such as paper, are well known. For example, U.S. Pat. No. 3,471,698, discloses an infrared absorption analyzer for detecting, on a reflecting surface, the presence of a thin film of a contaminant which has a defined infrared absorption band. Radiation covering selected portions of the infrared spectrum is projected onto, and reflected from, the surface to be tested. The reflected radiation is monitored to determine the amount of radiation reflected in that wavelength band in which the contaminant to be detected has a strong infrared absorption, and the amount of infrared radiation reflected in an adjacent wavelength band in which the contaminant does not show a strong absorption. A comparison of the amount of radiation reflected in the two bands will give an indication of the amount of contaminant present on the surface.

A moisture analyzer, as described above, requires complex optical and sensing devices and is not suitable for use in clinical apparatus. Further, several structurally different types of slides are required for the various analytes, and each type of slide has a reflectivity different from the other types. Thus, in certain cases, the reflectivity of a wet slide of one type may be very close to the reflectivity of a dry slide of another type. The apparatus for detecting fluid on analysis slides must be able to correctly process signals from all types of slides.

SUMMARY OF THE INVENTION

It is an object of the present invention to overcome the above-described problems in prior-art devices, and to provide a novel method and apparatus for determining whether an analysis slide contains sufficient sample fluid to produce suitable test results. The invention is particularly applicable for use with different types analysis slides for the analysis of biological fluids in which there is a substantial variation in the structural characteristics of the slides.

In accordance with one aspect of the invention, there is provided apparatus for detecting a sample fluid containing a substantial portion of water on a test element, the element being of the type which is adapted to receive a predetermined quantity of sample fluid from a metering device and to produce a response proportional to a selected analyte in the fluid, the element being selected from more than one type, each type being for a particular analyte, the apparatus comprising: means for projecting radiation comprising wavelengths absorbed by water onto the element; sensor means for detecting the intensity of radiation within the absorption band of water received from the element and for producing an output proportional to the intensity, the sensor means being adapted to produce a first output from radiation received before fluid is metered onto the element and a second output after fluid is metered onto the element; and means for processing the outputs, the processing means including means for comparing the difference between the first and second outputs with a predetermined value which corresponds to a sufficient amount of fluid on the element and for producing a signal in the event the amount of fluid is not sufficient to produce a proper response.

In accordance with the present invention there is also provided a method for detecting a sample fluid containing a substantial portion of water on an analysis slide, the slide being of a type which is adapted to receive a predetermined quantity of sample fluid and to produce a response proportional to a selected analyte in the fluid, the slide being selected from more than one type, each type being for a particular analyte and having a defined range of reflectivity which varies between a relatively high reflectivity when the slide does not contain any fluid and a relatively low reflectivity after fluid has been deposited on the slide, the method comprising the steps of: (a) projecting radiation onto a dry slide before the metering of fluid thereon; (b) detecting the intensity of radiation within the absorption band of water reflected from the dry slide; (c) projecting radiation onto the slide after the metering of fluid thereon; (d) detecting the intensity of radiation within the absorption band of water reflected from the slide after the metering of fluid onto the slide; (e) comparing the difference between the intensity of radiation reflected from the dry slide and from the slide after fluid has been metered thereon with a predetermined value within the reflectivity range of the slide to determine if sufficient fluid has been metered onto the slide to produce a proper response.

In one embodiment of the invention, a radiation source is adapted to project a beam of radiation onto a surface of an analysis slide supported in the metering position, and a sensor is adapted to detect the intensity of radiation reflected from the slide surface and to produce an output proportional to the intensity. The sensor is adapted to produce a first output as a result of radiation projected on a dry slide and a second output from radiation reflected from a slide after fluid has been metered thereon. The difference between the first and second outputs is compared to a predetermined value within a range of values for the particular type of slide being used, so that a signal means can be actuated in the event the intensity of the signal is not within a predetermined value. In an alternative embodiment of the invention, means are provided for determining the volume of fluid deposited on the analysis slide.

The disclosed invention is particularly advantageous for use with analysis slides in which the reflectivity of the slide varies from one type of slide to the next. It can be used to determine if an adequate amount of fluid has been deposited on the slide as well as to predict the volume of fluid on the slide. Detection is made using a single wavelength band, and thus, complex optical and sensing devices are not required.

Other features and advantages will become apparent upon reference to the following Description of the Preferred Embodiments when read in light of the attached drawings.

BRIEF DESCRIPTION OF THE DRAWINGS

FIG. 2 is a partial perspective view of the metering apparatus used in the analyzer, and showing the position of the drop detector relative to the metering apparatus;

FIG. 3 is a perspective view of an analysis slide and the optical components of a top-reading drop detector;

FIG. 4 is an elevational view, partially in section and partially in perspective, of a 1. bottom-reading drop detector;

FIG. 6a is a diagram showing the signal processing means for the drop detector shown in FIG. 2, and FIG. 6b is a graph of the signal developed by the sensor means in FIG. 6a; and FIG. 7a is a diagram showing the signal processing means for the drop detector in FIG. 5, and FIGS. 7b and 7c show the signal developed by the sensor means in FIG. 7a.

DESCRIPTION OF THE PREFERRED EMBODIMENTS

The invention is described hereinafter in connection with an analyzer for performing quantitative chemical analyses of biological fluids, such as blood serum. However, the invention is not so limited, and it can be employed in other types of apparatus where it is necessary to detect fluid metered onto a plurality of different types of substrates.

One form of test element, or analysis slide, for use with the subject invention is disclosed in the commonly-owned U.S. Pat. No. 3,992,158, granted on Nov. 16, 1976. The test element disclosed in this patent is formed as a multi-layer element containing the necessary reagents for reaction with components of a biological fluid, such as blood serum, deposited thereon. Certain reactions colorimetrically produce a change in optical density in the element which is sensed by a reflectometer, the amount of light reflected from the element varying in accordance with the reaction and being indicative of the amount of a particular analyte present in the fluid.

Terms such as "up," "down," "lower," "vertical," "horizontal," and "bottom," as used herein, refer to the orientation of parts when the disclosed apparatus is positioned in its normal operating position.

Figure 1:
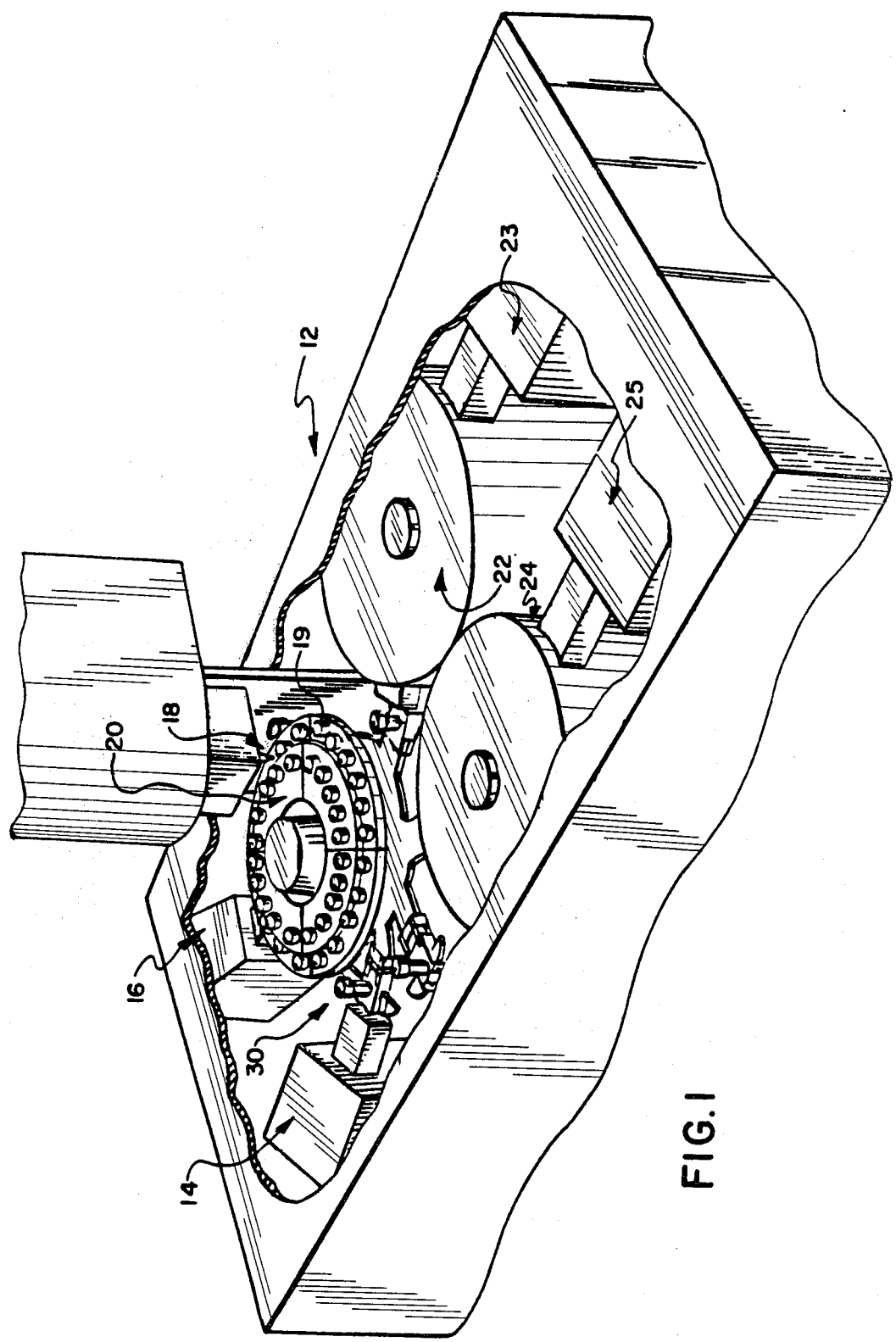
FIG. 1 is a perspective view of a chemical analyzer of the type which is adapted to employ the invention described herein.

In accordance with the preferred embodiment of the invention, there is shown in FIG. 1 an analyzer 12 of a type which is adapted to utilize test elements in the form of generally planar analysis slides. Analyzer 12 comprises a slide supply 14 for analysis slides 15 of the colorimetric type (FIG. 2), and a slide supply 16 for analysis slides of the potentiometric type (not shown). Metering apparatus 18 is adapted to aspirate sample fluid from a cup 19 supported in a sample tray 20 and to deposit a predetermined amount of the fluid onto an analysis slide supported in a slide distributor 30. A second metering device (not shown) works in conjunction with metering apparatus 18 to also deposit reference fluid on analysis slides of the potentiometric type. After the metering operation, slide distributor 30 deposits analysis slides of the potentiometric type in an incubator 22 and analysis slides 15 in an incubator 24. Incubators 22, 24, are adapted to cooperate respectively with analysis means 23, 25, for measuring a change in the analysis slides as a result of the fluids deposited thereon.

With reference to FIG. 2, metering apparatus 18 comprises a dispenser 40 having a dispenser head 46 which is adapted to receive a disposable metering tip 48 and is connected by means of a line 50 to a pump (not shown) of the positive displacement type. In the metering operation, a positioning means (not shown) for dispenser 40 is adapted to move the dispenser head 46 to a position over tray 20 where it is lowered to pick up a disposable metering tip 48; head 46 is then moved to a sample cup 19 where it aspirates in a supply of sample fluid. After aspiration of the sample fluid, dispenser head 46 is moved into a guide 116 on distributor 30 which locates the tip 48 relative to a slide 15 in the metering position. When the tip 48 has been located, the metering pump (not shown) is actuated for a preselected period to meter the desired amount of sample fluid onto the analysis slide 15. Tip 48 remains in the metering position for about 1/10 of a second after the metering pump stops to complete the metering operation, then, dispenser 40 is raised to a home position, shown in FIG. 2. In most cases, more than one analysis is performed on a particular sample fluid. If additional analyses are being performed, the dispenser 40 will be raised and lowered for each new slide. After the desired amount of sample fluid has been dispensed, used tips 48 are ejected into a container 110.

With reference to FIG. 2, the drop detector 60 of the subject invention comprises a source of radiation in the form of a miniature incandescent lamp 62 having a lens end 63; lamp 62 is adapted to project a beam of radiation, designated by arrows 64, onto the bottom surface of analysis slide 15. A sensor 66 is adapted to receive reflected radiation, designated by arrows 68, from slide 15. Sensor 66 is a photoelectric cell of the lead sulfide (PbS) type and is equipped with an integral notch filter (not shown) which passes infrared radiation at a wavelength of 1.945 microns. Radiation at a wavelength of 1.945 microns lies within the absorption band of the water, or moisture, contained in a slide 15. Thus, wet slides are characterized by a relatively weak output of the sensor 66 because the radiation is absorbed by the aqueous sample. The sensor 66 and lamp 62 are oriented relative to slide 15 to receive diffuse reflection from slide 15 and to minimize the specular reflection returned to the sensor 66.

Drop detector 60 detects moisture equally well, viewing from the top or from the bottom of slide 15. Limitations imposed by the analyzer dictate which location is more desirable. The analyzer 12 is configured such that a slide may be viewed dry, that is prior to the metering of sample fluid on the slide, most conveniently by a detector located under a slide 15 in the metering position. A second reading, after the metering operation, may be taken by the same sensor. There is an advantage to being able to compare readings taken before and after fluid has been metered onto slide 15. Slides 15 for different tests have different structural features that change their reflectivity. It is not always possible to distinguish the sensor output produced by a wet slide of one type from the output from a dry slide of another type. Comparing the first reading (dry) to the second reading (wet) on each slide eliminates the effect of the different reflectance characteristics of the various types of slides.

Figures 6A, 6B:
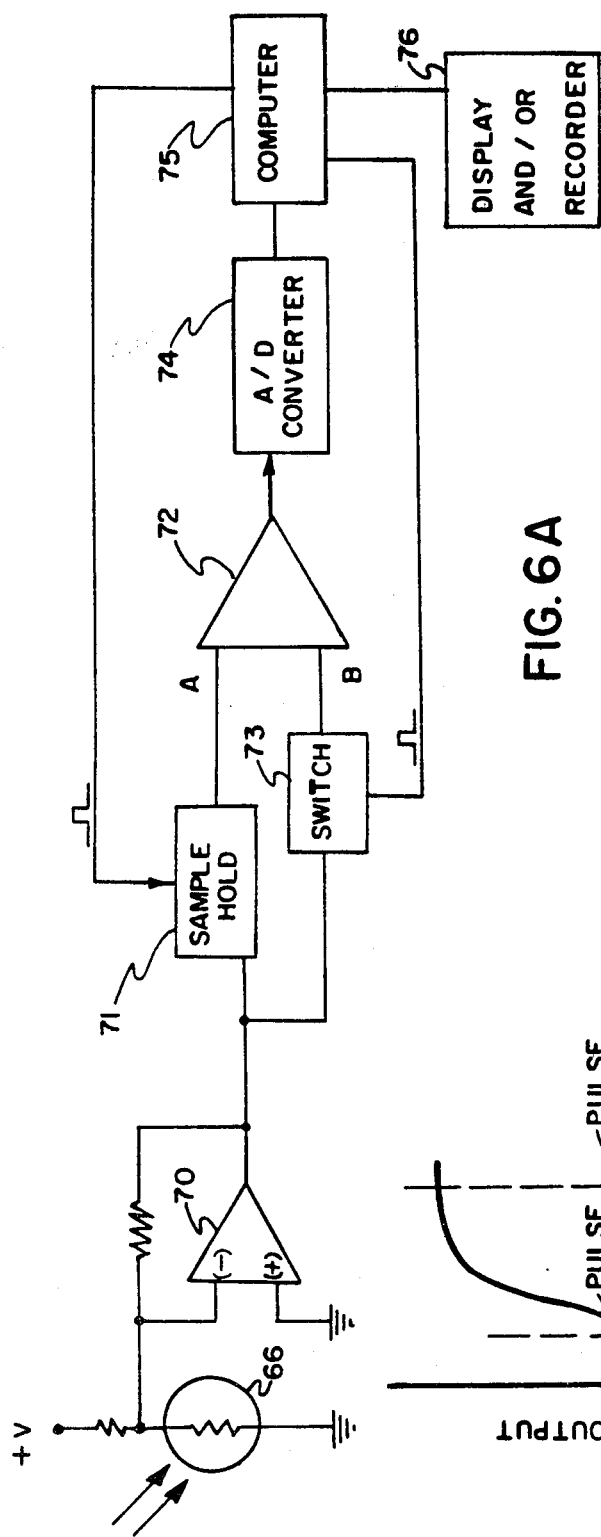

With reference to FIG. 6a, there is shown a means for processing the output from sensor 66. When the resistance of sensor 66 is low, the output delivered to amplifier 70 will be relatively low, as shown at A (dry reading) in FIG. 6b. The output A from amplifier 70 for the dry reading is delivered to a sample-and-hold circuit 71 where the output is stored as the result of a trigger pulse from a computer 75. After fluid has been metered on slide 15, radiation reflected from the slide 15 will be less, the resistance of sensor 66 will increase, and the output delivered to amplifier 70 will increase, as shown at B (wet reading) in FIG. 6b. At the appropriate time in the measurement cycle, computer 75 will allow the dry reading stored in the sample-and-hold circuit 71 to appear at input A of a differential amplifier 72, and simultaneously, a trigger pulse from computer 75 to switch 73 will deliver the present output of amplifier 70 (wet reading) to input B of amplifier 72.

Amplifier 72 receives inputs A and B and produces an output which is proportional to the difference between the wet and dry readings; this output is delivered to an analog-to-digital converter 74 which produces a digital signal which is fed to a computer 75. The computer 75 compares the difference between wet and dry readings with a stored value to determine if sufficient fluid has been metered on the slide. In the event sufficient fluid has not been metered onto the slide 15, the computer 75 warns the operator of a defective slide by means of a signal to a display device 76.

Computer 75 can be, for example, a programmable microcomputer of a conventional type. The instructions and method of programming such computers are well known in the art, and thus, no further explanation is considered necessary. It will be apparent to those skilled in the art that the output from amplifier 72 could also be fed to a comparator (not shown) which could produce an output directly to display device 76 if predetermined conditions were not satisfied.

An alternative embodiment of the invention is shown in FIG. 3 in which a drop detector 60a comprises a lamp 62a and a sensor 66a which are located above the slide 15. In this embodiment, the slide can be viewed in motion. The diameter of the spotted area 78, which is proportional to the volume of sample fluid, determines the duration of the wet signal produced by sensor 66a. Quantitative estimates of the drop volume can be performed by the computer 75. Information is included in the computer software to distinguish the various types of slides. The type of slide must be identified to the computer to allow interpretation of the signal of sensor 66a.

Another embodiment of the invention is shown in FIG. 4 in which a drop detector 60b comprises a lamp 62b and a sensor 66b, arranged as shown in FIG. 2. An auxiliary radiation source in the form of a lamp 80 has been arranged to project a beam of radiation onto the top of the slide 15, for reasons which will be discussed hereinafter. A filter which passes infrared radiation can be incorporated in sensor 66b, as in sensors 66 and 66a, or the filter can be a separate element, as shown at 79 in FIG. 4. Some types of the analysis slides 15 have been designed with layers that are translucent, rather than with the usual opaque white layer. The effect has been to reduce the signal returned to the sensor from a dry slide. The radiation energy is not reflected, but is partially transmitted through the slide. Thus, the signal difference between the wet and dry readings is small. The small signal difference is the same difference associated with very small (3 microliter) drops of slides of a highly-reflective type. If the analyzer is set to accept this small signal difference as representing a good drop on the translucent slides, very small drops on other slides will also be accepted. It is desirable to distinguish drops that are 6 microliters, or larger, from drops that are less than 6 microliters; the limit is arbitrary and could be set higher, depending on the sensitivity of the detector.

Lamp 80 is provided to focus light on the top surface of a slide 15 of the type which is translucent. The radiation from lamp 80 passing through the translucent slide, in addition to radiation from lamp 62b reflected from the slide, gives a dry reading comparable to a dry slide of a highly-reflective type. When the sample fluid is added to the slide, radiation from both lamps 62b and 80 is absorbed, and the sensor 66b responds with a wet reading comparable with a wet reading from a highly-reflective type of slide. The embodiment shown in FIG. 4 could also operate solely in a transmittance mode, i.e. without lamp 62b, at least with slides having translucent layers as described above. In such an arrangement, sensor 66b would be responding only to radiation transmitted through the slide.

Figure 5:
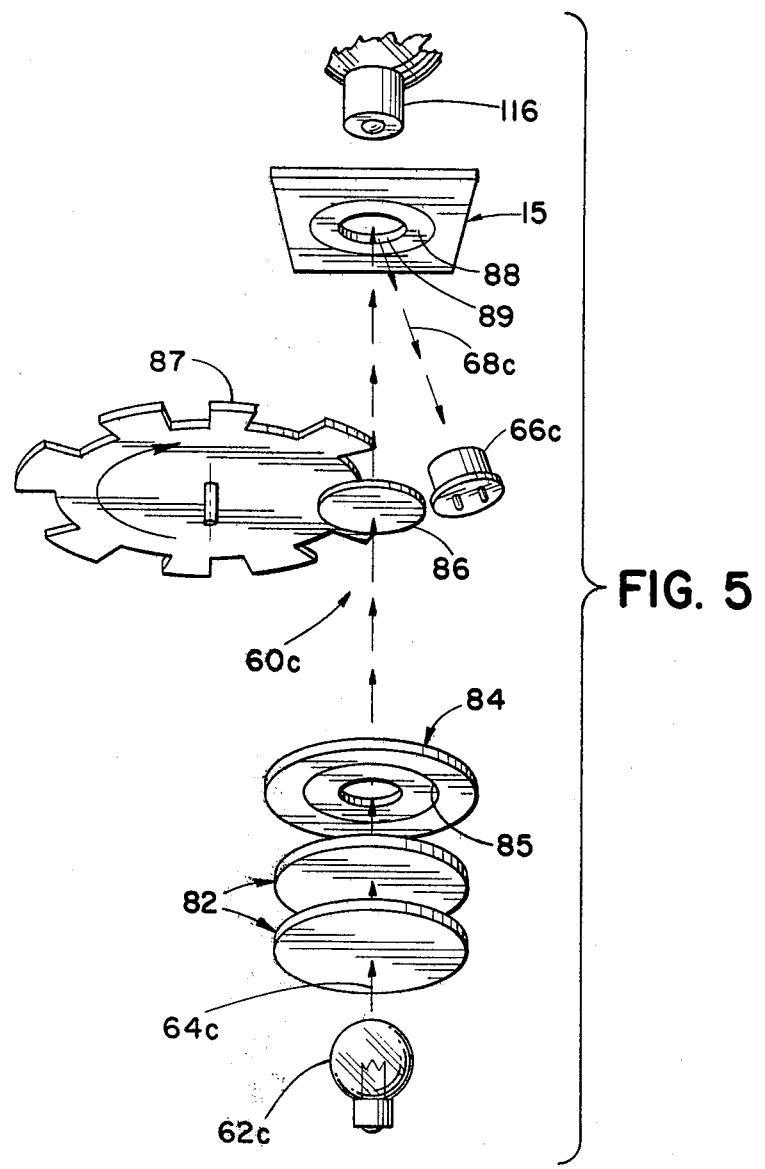
FIG. 5 is a schematic view of the optical system of another embodiment of the present invention.

Another embodiment of the invention is shown schematically in FIG. 5. A drop volume detector 60c comprises a lamp 62c which projects radiation in the direction of arrows 64c through condensing lenses 82 which image the lamp filament into the plane of the imaging lens 86. The beam of radiation is defined by a plate 84 having an annular opening 85. Imaging lens 86 focuses the beam onto the slide 15, creating the annular illuminated area 88 shown on slide 15 in FIG. 5. An optical chopper 87 rotatably driven by a motor (not shown) interrupts the beam near the imaging lens 86. The reflected radiation, designated by arrows 68c, is viewed by sensor 66c which produces an output proportional to the intensity of the reflected radiation. Optical chopper 87 causes a pulsating output to be produced by sensor 66c.

The operation of detector 60c depends on the principle that the area of the slide 15 wetted by the sample fluid is proportional to the volume of the sample fluid on the slide. Sensor 66c, which is a lead sulfide cell with an integral narrow band filter (not shown), responds selectively to 1.945 micron wavelength energy. Water in the applied samples strongly absorbs radiation at 1.945 micron wavelengths. The detector 60c is located in the metering station of the analyzer 12 so that a reading may be taken before and after the sample is metered. The amount of energy reflected to the sensor 66c is proportional to the dry area of the slide viewed by the sensor 66c. The output after the sample is dispensed is compared to the output prior to dispensing the sample. The output difference is proportional to the volume of sample on the slide. Apertures define the light beam illuminating the underside of the analysis slide so that an annular area, centered on the slide center is illuminated. The darkened area 89 in the center is sized so that unacceptably small drops fall completely in this shadow area. If no signal difference between wet and dry is observed, then the slide is rejected as a "dry" slide. Signal processing must include the identification of the slide type in order to correctly interpret the signal and correctly predict sample volume.

With reference to FIG. 7a, there is shown a means 67c for processing the signal developed in drop detector 60c (FIG. 5). The output from sensor 66c has an AC component having a waveform, shown at 91, and a frequency determined by light chopper 87. The voltage across sensor 66c is monitored by an amplifier 90, with the DC component removed by a capacitor 92 in series with the input to amplifier 90.

The output of amplifier 90 varies between a relatively strong signal for a dry slide and a relatively weak signal for a wet slide, as shown in FIG. 7b. The output from amplifier 90 is fed to an RMS/DC converter 93 which converts the pulsating signal into a continuous signal, as shown in FIG. 7c. The output from converter 93 for the dry reading goes to a sample and hold circuit 94. Suitable pulses from a computer 96 to the sample-and-hold circuit 94 and a divider circuit 95 will feed both dry (A') and wet (B') signals to the divider circuit 95 which produces an output which represents a ratio equal to the difference between the dry and wet signals divided by the dry signal. This ratio is delivered to an analog-to-digital converter 97 which feeds the signal in digital form to computer 96. The ratio for each slide is compared by the computer 96 to stored values for a particular type of slide, and a volume of sample fluid is predicted based on the ratio developed.

In the embodiments of applicants' invention described above, wet and dry readings are taken on each slide; this insures that the detector will operate properly over the entire range of reflectivity for each of the different types of slides 15. Under optimum conditions and with suitable programming of the computer, it is possible, with at least a number of similar types of slides, for a determination to be made as to whether sufficient fluid had been metered onto a slide, without first taking a dry reading of the slide. Reflectance values over the entire range from dry to wet would be stored in the computer for each type of slide, and the wet reading of the slide would be compared to the stored values.

The invention has been described in detail with particular reference to preferred embodiments thereof, but it will be understood that variations and modifications can be effected within the spirit and scope of the invention.

What is claimed is:

1. Apparatus for detecting a sample fluid containing a substantial portion of water on a test element adapted to receive a predetermined quantity of the sample fluid from a metering device and to produce a response proportional to a selected analyte in the fluid, an element being of a type for the selected analyte and having certain reflectance characteristics, said apparatus comprising:

means for projecting a beam of radiation comprising wavelengths absorbed by water onto a surface of a test element;

sensor means for detecting the intensity of radiation within the absorption band of water reflected from a surface of a test element and for producing an output proportional to said intensity, said sensor means being adapted to produce a first output from radiation received before fluid is metered onto an element and a second output after fluid is metered thereon; and means for processing said outputs, said processing means including means for receiving an input indicative of the reflectance characteristics of said type of test element and for comparing the difference between said first and second outputs with a predetermined value which corresponds to a sufficient amount of fluid on said type of test element, and means for producing a signal in the event the amount of fluid is not sufficient to produce a proper response.

2. Apparatus, as defined in claim 1, wherein said means for projecting a beam of radiation is an incandescent lamp having a lens end.

3. Apparatus, as defined in claim 1, wherein said sensor means includes a lead sulfide cell having an integral notch filter which passes a narrow band of radiation which includes a wavelength of 1.945 microns.

4. Apparatus, as defined in claim 1, wherein said means for projecting a beam of radiation and said sensor means are positioned above an element.

5. Apparatus, as defined in claim 1, wherein said means for projecting a beam of radiation and said sensor means are positioned below an element.

6. Apparatus, as defined in claim 5, wherein means are provided for projecting a beam of radiation on a top surface of an element, and said sensor means detects the intensity of radiation transmitted therethrough.

7. Apparatus, as defined in claim 1, wherein means is provided for supporting an element for movement relative to said sensor means, and said processing means is adapted to integrate the output received from said sensor means as an element is moved relative to the sensor means and to predict a drop volume based thereon.

8. Apparatus, as defined in claim 1, wherein said means for projecting a beam includes means for projecting an annular image onto a surface of a test element, and the interior diameter of said image is sized according to a desired quantity of sample fluid.

9. Apparatus, as defined in claim 8, wherein the means for processing said outputs comprises means for predicting drop volume based on said outputs.

10. A method for detecting a sample fluid containing a substantial portion of water on an analysis slide, said slide being adapted to receive a predetermined quantity of sample fluid and to produce a response proportional to a selected analyte in the fluid, said slide being selected from more than one type, each type being for a particular analyte and having a defined range of values of reflectivity which varies between a relatively high reflectivity when the slide does not contain any fluid and a relatively low reflectivity after fluid has been deposited on the slide, said method comprising the steps of:

(a) projecting radiation comprising wavelengths absorbed by water onto a dry slide before the metering of fluid thereon;

(b) detecting the intensity of radiation within the absorption band of water reflected from said dry slide;

(c) projecting radiation comprising wavelengths absorbed by water onto said slide after the metering of fluid thereon;

(d) detecting the intensity of radiation within the absorption band of water reflected from said slide after the metering of fluid onto the slide;

(e) comparing the difference between the intensity of radiation reflected from said dry slide and from said slide after fluid has been metered thereon with a predetermined value within the reflectivity range of the type of slide suitable for said selected analyte to determine if sufficient fluid has been metered onto the slide to produce a proper response; and (f) producing a signal in the event the amount of fluid is not sufficient for a proper response.

11. A method, as recited in claim 10, wherein the intensity of said radiation is detected in the infrared region.

12. A method, as recited in claim 10, wherein said radiation is projected onto the slide to form an annular image, and the interior diameter of the image is sized according to a desired quantity of sample fluid.

13. Apparatus for determining the volume of fluid on an analysis slide which is one of a plurality of types, each type being for a particular analyte and having a defined range of values for reflectivity, said apparatus comprising:

a radiation source for projecting a beam of radiation comprising wavelengths absorbed by water onto a defined area of a surface of a slide;

sensor means for detecting the intensity of radiation reflected from said area and for producing an output proportional to said intensity, said sensor means being adapted to produce a first output from radiation received from said area before fluid is metered onto a slide and a second output from radiation received from the area after fluid is metered onto a slide; and means for processing said first and second outputs, said processing means including means for storing the range of values which corresponds to the type of slide and for receiving an input indicative of the type of slide, and said processing means having means for comparing the difference between said first and second outputs with the stored range of values and for predicting the volume of fluid on a slide based on the value of said difference.

14. Apparatus, as defined in claim 13, wherein said radiation source is a lamp which produces radiation in the spectral band which includes 1.945 microns.

15. Apparatus, as defined in claim 13, wherein means which includes an annulus is interposed between said source and a slide and said defined area is annular.

16. Apparatus, as defined in claim 13, wherein an optical chopper is interposed between said source and a slide.

17. Apparatus for detecting a sample fluid containing a substantial portion of water on a test element adapted to receive a predetermined quantity of sample fluid from a metering device and to produce a response proportional to a selected analyte in the fluid, an element being selected from more than one type, each type being for a particular analyte, said apparatus comprising:

means for projecting a beam of radiation comprising wavelengths absorbed by water onto a surface of an element;

sensor means for detecting the intensity of radiation within the absorption band of water reflected from a surface of an element and for producing an output proportional to said intensity, said sensor means being adapted to produce an output after fluid is metered onto a test element; and means for processing said output, said processing means including means for receiving an input indicative of the type of element and for comparing said output with a predetermined value corresponding to a reflectivity which represents a sufficient amount of fluid on a test element, and said processing means having means for producing a signal in the event the amount of fluid is not sufficient to produce a proper response.

18. Apparatus for detecting a sample fluid containing a substantial portion of water on a test element, said element being adapted to receive a predetermined quantity of sample fluid from a metering device and to produce a response proportional to a selected analyte in the fluid, an element being selected from more than one type, each type being for a particular analyte, said apparatus comprising:

means for projecting radiation comprising wavelengths absorbed by water onto an element;

sensor means for detecting the intensity of radiation within the absorption band of water received from an element and for producing an output proportional to said intensity, said sensor means being adapted to produce a first output from radiation received before fluid is metered onto an element and a second output after fluid is metered onto an element; and means for processing said outputs, said processing means including means for receiving an input indicative of the type of element and for comparing the difference between said first and second outputs with a predetermined value which corresponds to a sufficient amount of fluid on an element, and said processing means having means for producing a signal in the event the amount of fluid is not sufficient to produce a proper response.

19. Apparatus, as defined in claim 18, wherein said means for projecting radiation comprises means for projecting a beam of radiation onto an element, and said sensor means detects the intensity of radiation transmitted therethrough.

20. Apparatus, as defined in claim 18, wherein said means for projecting radiation comprises means for projecting a beam of radiation on one surface of an element, and said sensor means detects the intensity of radiation reflected therefrom.

* * * * *